United States Patent [19]

Rowland

[11] 4,189,725
[45] Feb. 19, 1980

[54] BATTERY POWERED CONDITION SENSING AND DISPLAY APPARATUS WITH LOW BATTERY INDICATION

[75] Inventor: Robert O. Rowland, Hemet, Calif.

[73] Assignee: Hudson Oxygen Therapy Sales Company, Temecula, Calif.

[21] Appl. No.: 795,386

[22] Filed: May 10, 1977

[51] Int. Cl.² ............... G08B 21/00; G08B 17/10
[52] U.S. Cl. ............................. 340/636; 73/23; 340/632
[58] Field of Search ............... 340/249, 632, 633, 634, 340/636; 73/23

[56] References Cited
U.S. PATENT DOCUMENTS

| | | | |
|---|---|---|---|
| 3,802,182 | 4/1974 | Fujita | 340/249 X |
| 4,010,456 | 3/1977 | Erni | 340/249 X |
| 4,024,415 | 5/1977 | Matsuura | 340/249 X |
| 4,041,691 | 8/1977 | Chihara et al. | 340/249 X |
| 4,074,515 | 2/1978 | Asano | 340/249 X |

Primary Examiner—John W. Caldwell, Sr.
Assistant Examiner—Daniel Myer
Attorney, Agent, or Firm—John E. Wagner; Jerry R. Seiler

[57] ABSTRACT

A condition monitoring system such as a hospital oxygen monitoring and analyzing device which is battery powered and of such low current drain circuitry that the monitor may be maintained ON continuously. The circuitry senses battery condition when the end of battery life is approaching as indicated by terminal voltage drop. The circuitry continues to provide an accurate display but also indicates a part of the display and additional symbol. The circuitry provides a separate indication under calibration conditions, and the improved voltage regulator includes a transistor back biased to breakdown as the regulation device. A remote sensor is used and engaging the sensor with the unit, automatically powers all circuitry.

5 Claims, 9 Drawing Figures

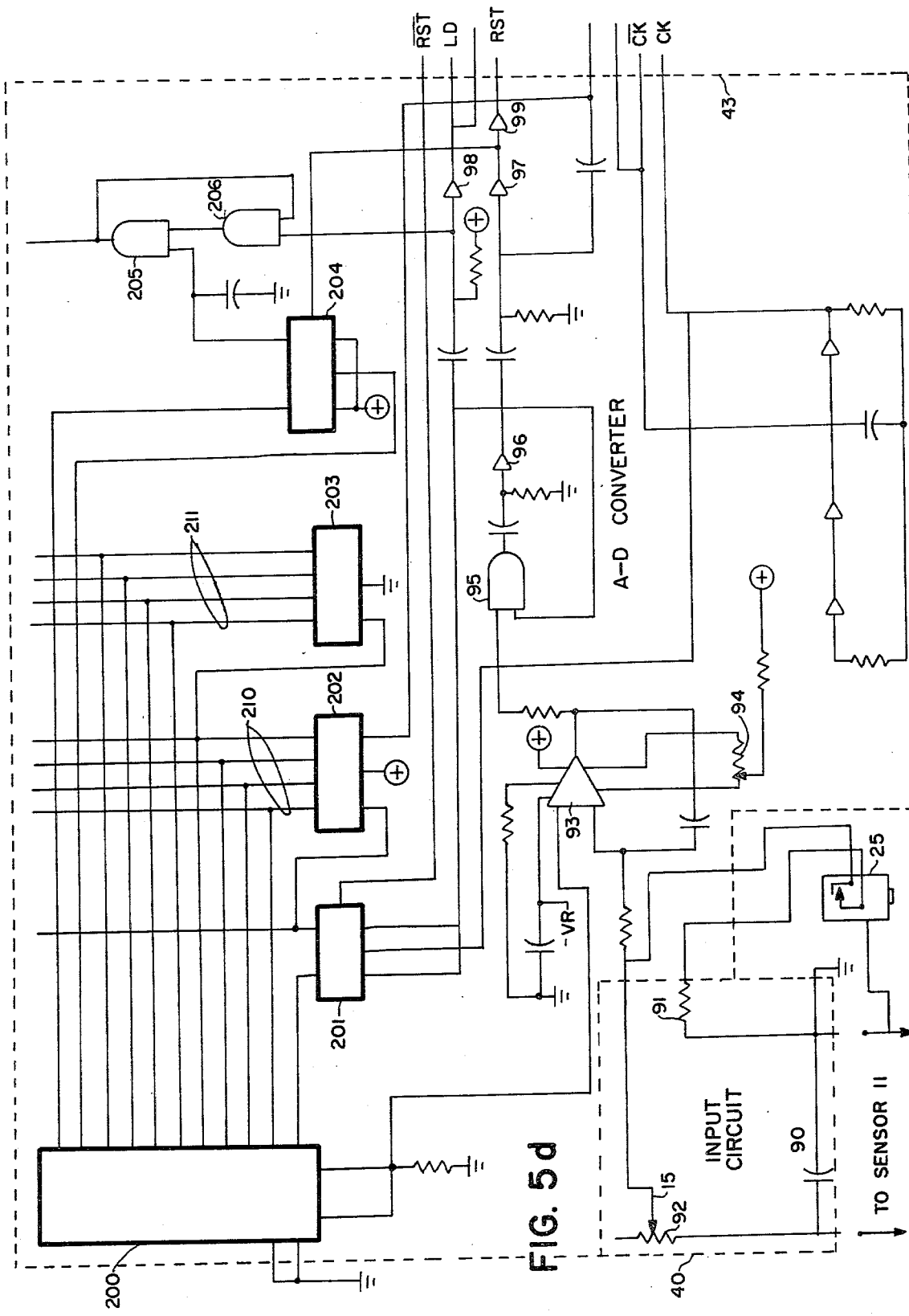

BATTERY POWERED CONDITION SENSING AND DISPLAY APPARATUS WITH LOW BATTERY INDICATION

BACKGROUND OF THE INVENTION

Condition monitoring equipment such as oxygen monitors for hospital use have long employed AC powered circuitry, micro fuel cells and meter indicators. More recently hospital monitoring equipment has been battery powered, where possible, to avoid the exposure of patients to an alternating current environment whenever possible. This has been important particularly in the oxygen therapy field where increased levels of oxygen can be associated with explosion and fire danger, and in the case of electrically sensitive patients, e.g. those with implanted electrodes, pace-makers and the like. Examples of battery powered medical equipment are disclosed in U.S. Pat. Nos. 3,785,207 and 3,765,244 to J. Brzezinski, and examples of battery powered oxygen monitoring equipment is disclosed in U.S. Pat. No. 3,375,700 to R. Hubner.

Typically, such equipment to provide accurate reading must regulate the power supply and such is accomplished in the Brzezinski patents referenced above employing zener diodes. I have discovered however that the current drain of the zener diode in providing voltage regulation is excessive and I have therefore proceeded to develop a non-zener diode regulation circuit which is simple and of low current drain.

It has been the practice in recent years in battery powered electronic equipment to provide a battery condition indicator. Such a condition indicator in oxygen monitoring equipment is shown in U.S. Pat. No. 3,375,700. The battery condition indication, however, is independent of the displayed data.

I have further discovered that the typical meter employed to register a condition such as oxygen concentration at best has an accuracy in the order of 1 to 2 percent in actual reading. Also, because of parallax and other problems of the sensitivity of meter reading, quite often the error in the actual reading recorded or noted may be easily 5%. Under such conditions, the accurate, precise monitoring of a condition such as oxygen concentration is impractical if not impossible.

In the past, medical equipment including alarm circuits when a parameter exceeds a limit, has been employed. I have discovered, however, that most of such alarm circuits are of an analog nature and and that the error inherent in or resulting in the limit circuit may be significantly greater than the sensing accuracy. In such case, the very condition which one seeks to eliminate may occur and the user has a false sense of security because of the monitoring and limit functions provided by the equipment.

BRIEF DESCRIPTION OF THE INVENTION

The oxygen monitor and analyzer of this invention are battery powered and of extremely low current design thereby allowing continuous monitoring of the oxygen content of an atmosphere up to 100% concentrations. Battery condition is continuously monitored and a visual indication is given as the batteries approach the end of useful life. The battery condition indication is a part of the visual display of oxygen concentration and given along with an accurate reading whereby the user necessarily notes battery condition with each reading taken.

A regulated power supply is employed which insures accuracy in the sensing, signal, processing and display circuitry with a minimum power consumption in the regulation circuit itself. This circuit employs a transistor which is back biased to provide precise regulation with minimum current drain.

Signal processing including alarm setting levels and display is on a digital basis from the sensor input on for improved accuracy.

The display employs liquid crystals providing an easily read digital indication of the percent oxygen to accuracy limited by the sensor.

BRIEF DESCRIPTION OF THIS DRAWING

This invention may be more clearly understood from the following detailed description and by reference to the drawings in which.

Figure 5A:
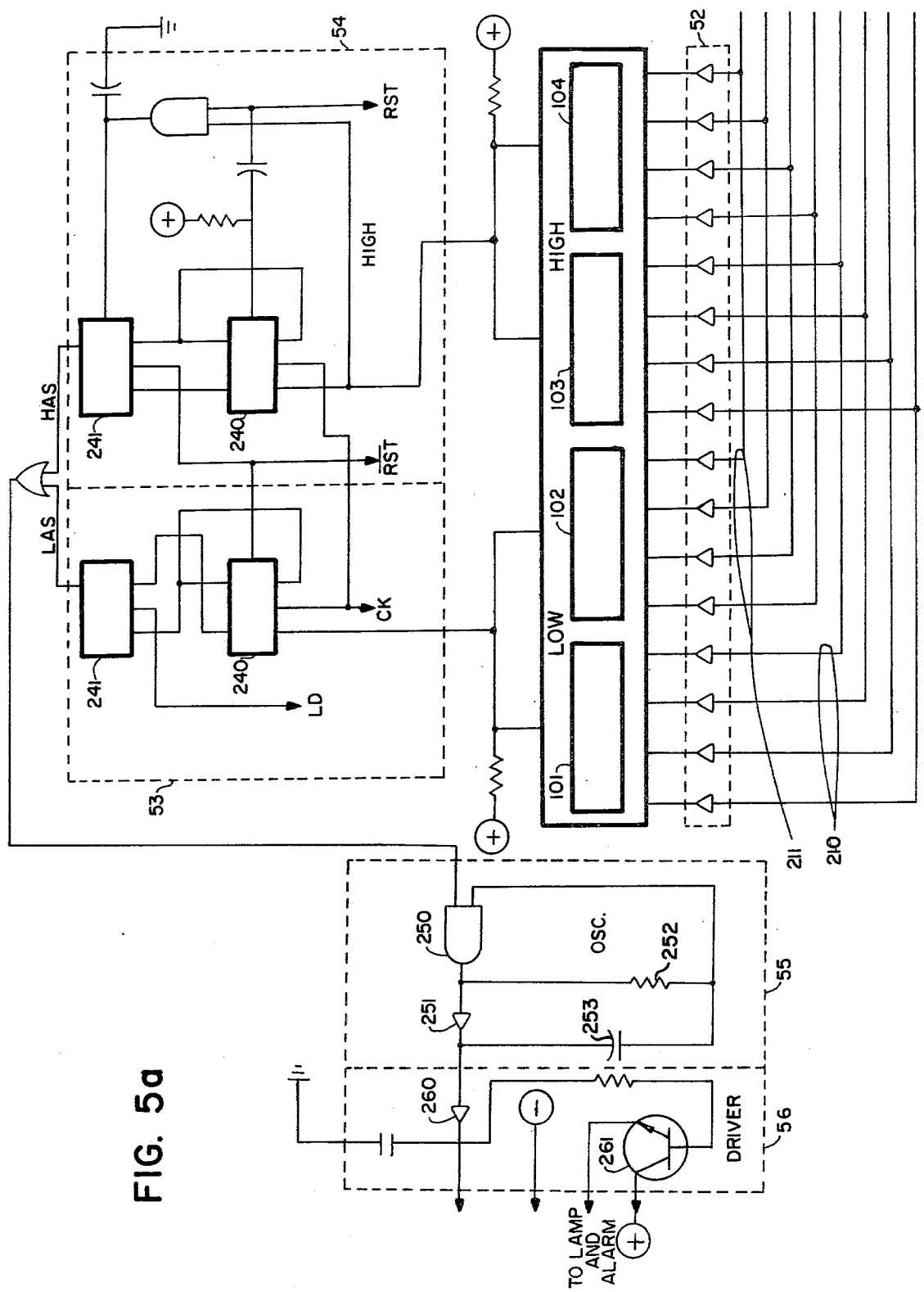
Figure 5B:
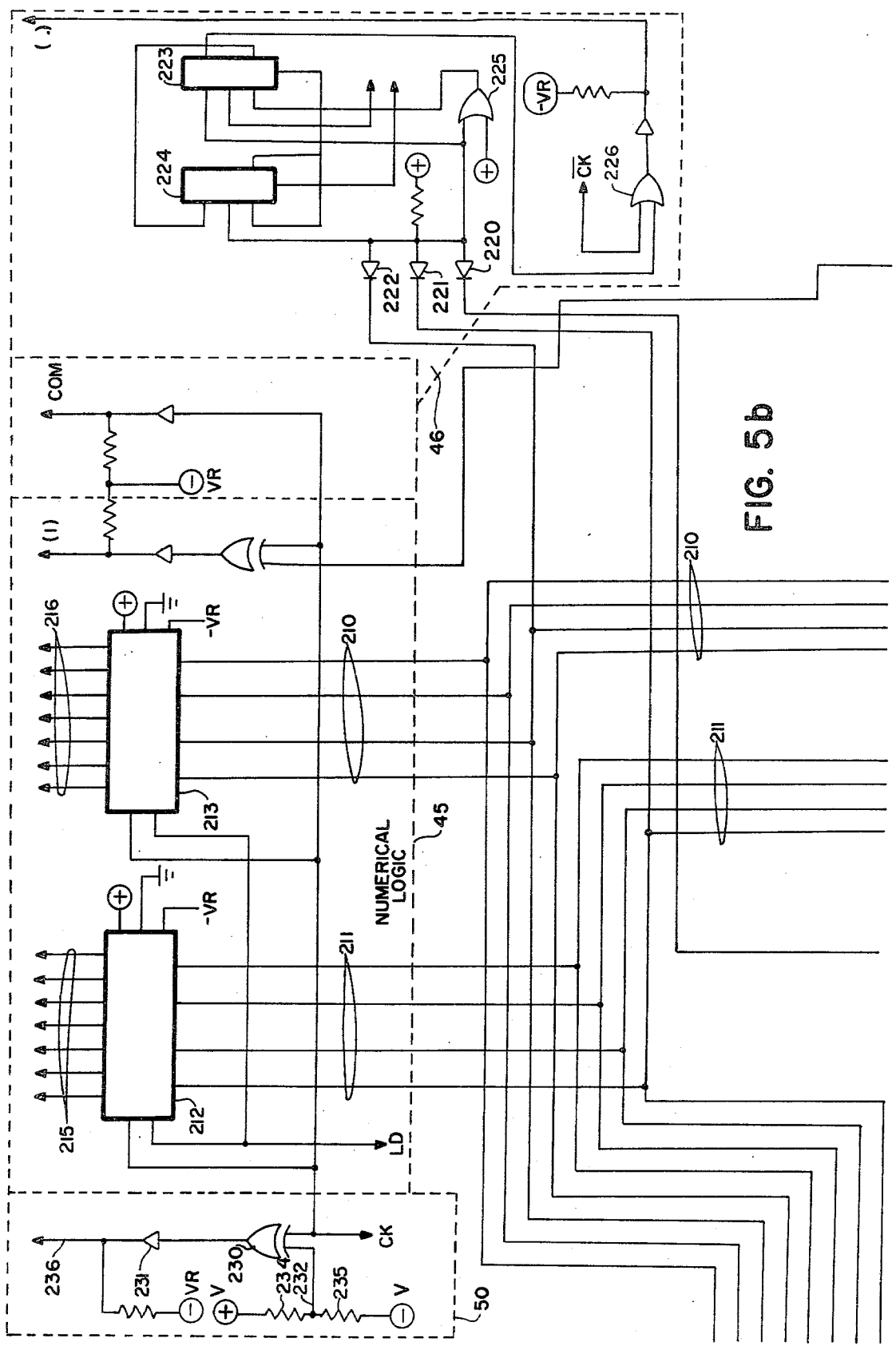
Figures 5C, 6:
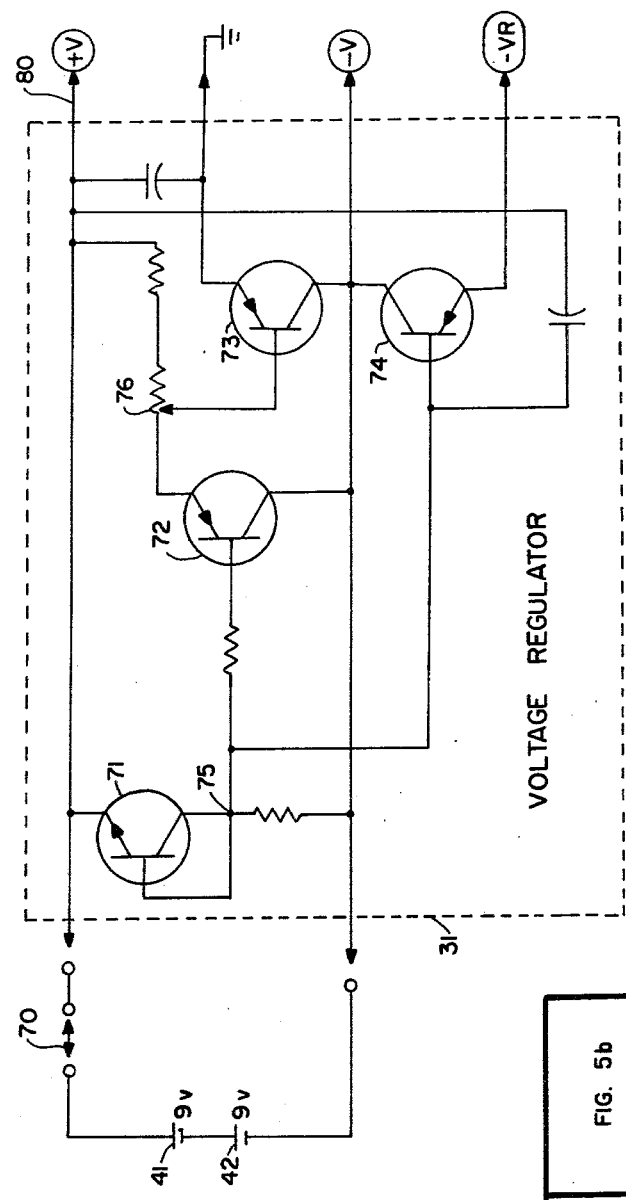

FIGS. 5a, 5b, 5c and 5d constitute an electrical schematic diagram of this invention; and FIG. 6 is a layout diagram of FIGS. 5a–d.

DETAILED DESCRIPTION OF THIS INVENTION

Figure 1:
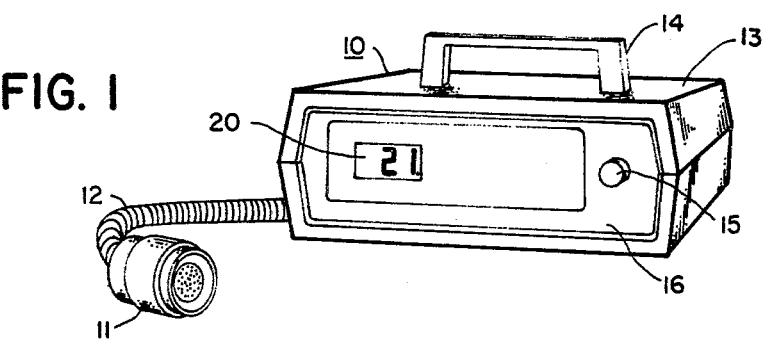
FIG. 1 is a perspective view of a digital oxygen analyzer in accordance with this invention.
Figure 2:
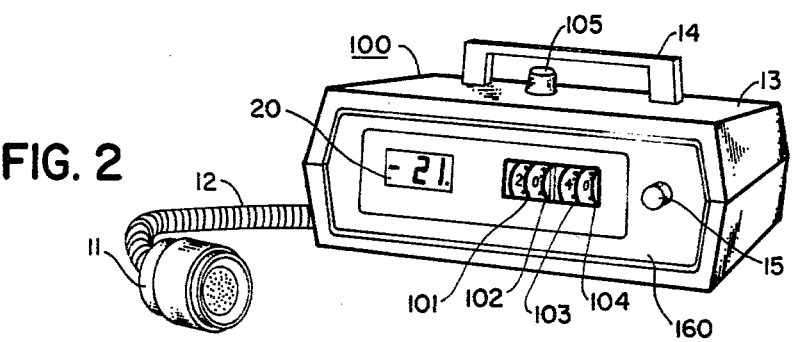
FIG. 2 is a perspective view of a digital oxygen monitor in accordance with this invention.

Now referring to FIGS. 1 and 2, two related embodiments of this invention may be seen therein. In FIG. 1, a portable oxygen analyzer 10 employing a sensor 11 is connected to the oxygen analyzer 10 by a flexible extensible cable 12. The analyzer 10 itself is contained within a housing 13 and may be transported by handle 14 to positions where monitoring is required, for example in an oxygen rich enclosure used for oxygen therapy for medical patients, or in industrial or chemical process applications provided they are conducted in the operating temperature and pressure range of the analyzer, namely 32° F. to 120° F. and ambient air pressures.

The analyzer 10 of FIG. 1 has only a single external control, a calibrate knob 15 located on the front panel 16. Also appearing on the front face is an indicator 20 comprising a liquid crystal panel having five positions, a negative sign, 3 digit spaces and a decimal point, the significance of each becoming more apparent in the description below. As shown in FIG. 1, the indicator 20 registers 21% oxygen (normal atmosphere). When 21% oxygen is registered the decimal point appears to the right of the digits, thus (21.). It may be seen that the analyzer 10 presents an uncluttered instrument panel with only a calibration control, used only periodically and a clear visual indicator which requires only direct viewing and recording if required with little interpretation being required.

The oxygen monitor 100 in accordance with this invention appears in FIG. 2. It resembles the oxygen analyzer 10 of FIG. 1 in external appearance and throughout this description the same reference numerals indicate identity on both embodiments. Elements found only in the oxygen monitor 100 are identified by a reference numeral in the 100 series.

Most notable on the exterior of the oxygen monitor 100 are two pair of thumbwheel switches, 101 and 102 for selecting a two digit number of the minimum allowable percentage oxygen concentration and 103 and 104 repeating the two digit maximum allowable percentage oxygen concentration. These thumbwheel switches display the values at which they are set and are adjustable in 1% increments, between 0° minimum and 100° maximum.

Also noticable on the top of the oxygen monitor 100 is a visual alarm red lamp 105 which is energized if either the minimum or maximum setting of switches 101-104 are passed. An audio alarm 106 appearing in FIG. 3 at the rear of the monitor 100 gives off a loud alarm which allows the attending personnel to make the necessary adjustment to the oxygen level.

In both the oxygen analyzer 10 or the monitor 100 the preferred sensors 11 are micro-fuel cells utilizing potassium hydroxide contained within an oxygen permeable membrane and in contact with the sensing face of a gold plated disc shaped cathode adjacent to a copper anode. The presence of oxygen in the electrolyte after penetrating the permeable membrane changes the electrical current generated by the micro fuel cell in direct proportion to the oxygen concentration. After processing through the circuitry of this invention, the percentage concentration may be displayed. Sensors of this type are known in the industry and available from commercial sources such as the C1 or C2 micro fuel cell of Teledyne Instruments of San Gabriel, Calif.

Micro-fuel sensors of this type have an accuracy of about ±1% and it is therefore essential for maximum accuracy of the entire instrument that all circuitry, power supply and display exhibit an accuracy greater than 1%. This is particularly important for the limit settings. In order to achieve the accurancy dependent upon the sensor, I have developed circuitry producing accuracy of ±0.5%.

Figure 3:
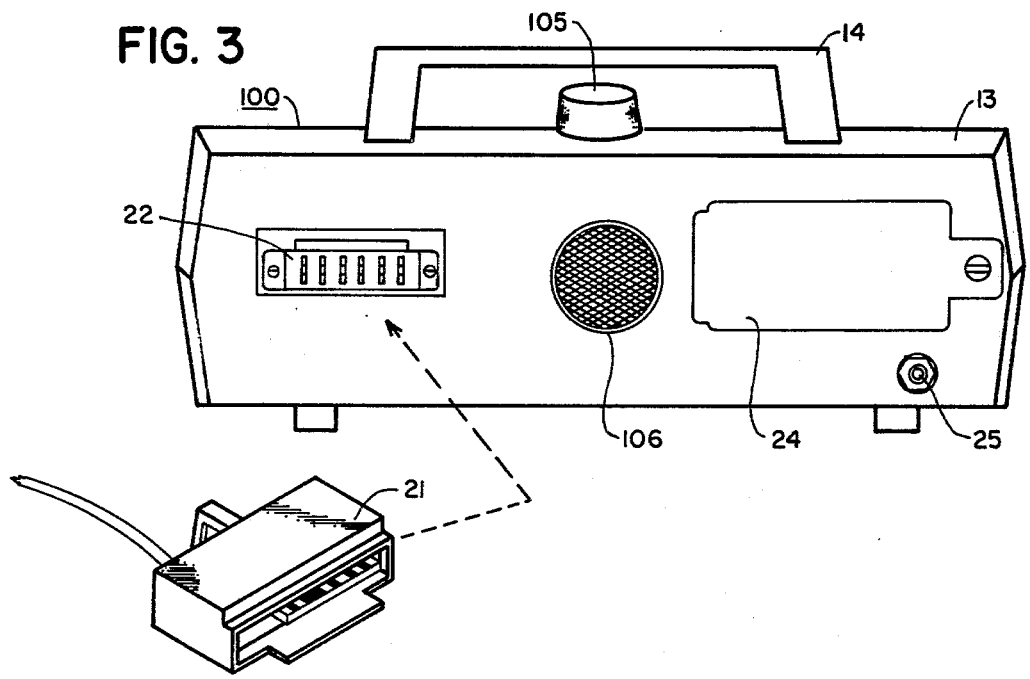
FIG. 3 is a rear view thereof.

The rear of the monitor 100 appearing in FIG. 3 illustrates the plug 21 on the sensor connecting lead 12 of sensor 11 and the mating socket 22 built into the monitor 100. Also appearing in FIG. 3 is the audible alarm 106 and the door 24 to the battery compartment in which the battery supply is located, e.g. two 9 v. Mallory MN1604 alkaline cells or the equivalent. A jack 25 for connecting the monitor 100 or analyzer 10 to an external recorder completes the complement of the rear face features.

Figure 4:
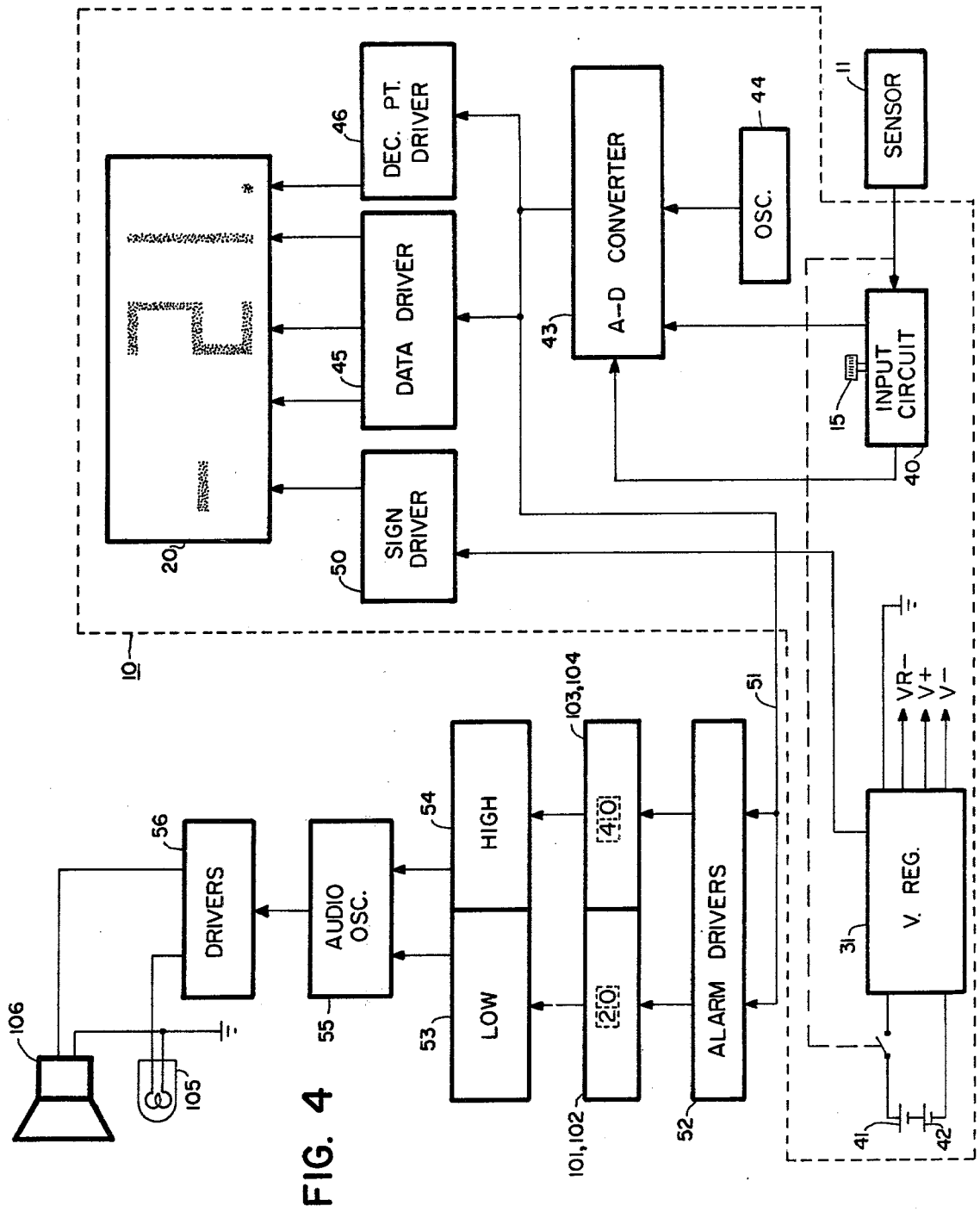
FIG. 4 is a block diagram of this invention.

The circuitry of this invention is illustrated in block diagram form in FIG. 4 in which the sensor 11 is connected to an input circuit 40 which references the signal voltage to ground and includes the calibration potentiometer controlled by knob 15 of FIGS. 1 and 2. The sensor also mechanically closes the power circuit from a pair of batteries 41 and 42 to a voltage regulator 31. This is accomplished easily by a shorting terminal in the plug 21 so that insertion of the plug 21 enables the monitor 100 or analyzer 10 and for continuous operation whenever the sensor 10 is connected to the instrument. This eliminates the possibility of the equipment being in position but turned off.

The oxygen concentration signal after passage through the input circuit 40 is introduced into an analog to digital converter 43 driven by an oscillator 44. After conversion to digital form the oxygen concentration signal is processed totally in digital form thereby eliminating the calibration, drift and tolerance problems normally associated with analog circuits, particularly analog reading meters.

The digitized signal form A-D converter 43 is introduced into data driver circuit 45 and decimal point driver circuit 46 which respectively generate the signals to drive a liquid crystal display indicator 20 to display the correct 2 or 3 digit numbers (0-99 and 100) and a decimal point following the units digit position.

An additional input to the liquid crystal display 20 is from a (−) sign driver signal generator 50 which monitors the terminal voltage of the batteries 41 and 42 and whenever the voltage drops from a nominal 18 v (9 v+9 v) to 10 v, the (−) sign driver circuit 50 energizes the liquid crystal display 20 to register a minus (−) sign preceding the % concentration signal. Note that the minus sign generator circuit 50 is independent of actual oxygen concentration signal generation except for having a common power supply and display. The oxygen concentration signal handling circuitry is designed to operate accurately at battery voltage as low as 7 v. Thus this invention gives an accurate reading of oxygen concentration for well after a minus (−) sign precedes the numerical display. The attendant thus receives a correct numerical value but an impossible value. This indicates that approximately 10% of the battery life is left and batteries should be changed now. If the attendant accurately records the value displayed or if an automatic recorder plugged into jack 25 also records the sign information (−), the reviewer of the data can be assured at all times that the equipment is operational and if batteries are needed when they are approaching the end of their useful life before it is reached. Typically battery life is 6 months for continuous use due to the unique battery saving features described below.

In the oxygen monitor version of FIGS. 2 and 3, the A-D converter 43 also drives the limit alarm circuitry through lead 51 to digital alarm driver circuit 52 connected to the thumbwheel switches 101-104. These switches allow the comparison of the digitally encoded actual value with the low and high limits set, and if the actual concentration is outside of the low or high limit, the low or high alarm circuits 53 or 54 are energized triggering an oscillator 55 which, through driver circuits 56 operate the visual indicator lamp 105 and the sonic alarm 106. The alarm circuitry remains operative until the oxygen concentration returns within limits or the batteries become exhausted by the visual and sonic alarm operation.

In FIG. 4 the distinction between the oxygen analyzer 10 and the oxygen monitor 100 is apparent by the enclosing dashed lines representing the oxygen analyzer 10 which excludes the limit circuitry and alarms. The monitor 100 employs the entire circuitry of FIG. 4.

DETAILED CIRCUITRY

A preferred embodiment of this invention appears in detail in FIGS. 5a-d showing a specific circuit which accomplishes all described above.

VOLTAGE REGULATOR (FIG. 5c)

The batteries 41 and 42 each exhibiting a nominal terminal voltage of 9 v are connected in series via switch or shorting plug 70, (a part of plug 21 of FIG. 3) to the voltage regulator 31. This circuit employs four discrete transistors 71-74. Transistor 71 is back biased to provide a reference voltage of about 6.5 v. to junction 75 in the base circuit of transistors 72 and 74. Adjustment of the potentiometer 76 establishes a voltage between −3.9 v and −4.2 v at the emitter junction of transistor 73 (unit ground) referenced to +v on lead 80. This is the supply voltage for the digital circuitry and the reference voltage for the A to D converter. The emitter of transistor 74 —VR is about —5.5 v referenced to +v. This is the minus supply for the liquid crystal display driver 45 and the comparator 93. The unregulated negative voltage —v is used to power both the sonic alarm 106 and the visual indicator lamp 105.

An important feature of this voltage regulator is that it regulates precisely within limits of ±3 mv while itself consuming less than 50 microamperes as compared with a conventional zener regulator which consumes 2 to 20 milliamperes.

INPUT CIRCUIT (FIG. 5d)

The sensor 11 of FIGS. 1 and 2 introduces its signal to the monitor through the input circuit 40 of FIG. 5d which comprises basically a precision RC network including a shunt capacitor 90 and a pair of series resistances, 91 and 92. Resistance 92 is adjustable and in fact is the calibration adjustment controlled by knob 15. Adjustable resistance 92 is used to compensate for differences in output from one cell to another. Variations in the internal resistance and age of the sensor 11 plus any drift of the analog element resistance 91 are thus compensated for in this circuit.

ANALOG TO DIGITAL CONVERTER (FIG. 5d)

Immediately after callibration in input circuit 40 the analog signal is introduced into A-D converter 43 at comparator stage 93. This comparator's offset is adjusted by potentiometer 94 which also establishes the zero point of the A-D converter. The comparator 93, in combination with the logic AND gate 95, CMOS integrated circuits 96 and 97, 98 and 99, as well as ladder resistor network 200 and integrated circuits 201–204 and AND gates 205 and 206 convert the analog input signal to BCD form with the least significant digit appearing on leads 210 and the most significant digit on leads 211. This circuit also generates synchronizing clock pulses $\overline{ck}$ and ck as well as reset pulses RST and $\overline{RST}$ and pulses LD. The A-D converter is not only significant in the generation of these signals but through the use of CMOS integrated circuits and the low power design draws only approximately 50 microamperes. The capability of this invention to operate continuously is due in a significant degree to the power efficiency of the A-D converter 43.

NUMERICAL LOGIC (FIG. 5b)

The binary coded decimal digits representing the oxygen concentration is introduced through upward extending branches of leads 211 and 210 to the numerical logic circuits 45 comprising a pair of integrated circuits 212 and 213 which act as memories for the display 20 of FIGS. 1 and 2. The outputs of these integrated circuits 212 and 213 are applied to the display and parallel leads 215 and 216 respectively to energize the display.

DECIMAL POINT LOGIC (FIG. 5b)

The least significant bit as stored in integrated circuit 201 of A-D converter 43, the least significant digit (1) from integrated circuit 202 and the most significant digit (2) from integrated circuit 203 are introduced into the decimal point logic circuit via reverse poled diodes 220, 221 and 222 respectively. When these are present in the respective memories, i.e. 21%±½% oxygen, the decimal point logic circuit 46 is enabled applying an energizing signal to the liquid crystal display indicator 20 of FIGS. 1, 2 and 4 to display the decimal point. At all other conditions the decimal point logic 46 disables the display of the decimal point. The decimal point logic circuit 46 employs integrated circuits 223 and 224 and NOR gates 225 and 226.

MINUS SIGN DIGITAL LOGIC (FIG. 5b)

One truly significant aspect of this invention is the circuitry which displays a clear indication of low battery condition without interfering with accurate data display. This is accomplished by the minus sign digital logic circuit 50 which employs the regulated voltage —VR as well as the positive and negative unregulated voltages +V and —V, a NOR gate 230 and integrated circuit 231. When the input circuit on lead 232 to NOR gate 230 is below 2.0 volts, the input of 231 is in phase with ck. If the voltage at the junction 232 between resistances 234 and 235 drops below a selected level representing, e.g. 10 v, integrated circuit 230 changes the phase of the input to integrated circuit 231 which in turn changes the phase of 236 causing the (—) sign to display on indicator 20.

OXYGEN MONITOR ALARM CIRCUIT (FIG. 5a)

The foregoing circuitry is common to both the oxygen analyzer 10 and monitor 100. The following circuitry is related to the alarm circuitry of the oxygen monitor 100. This is found specifically in FIG. 5a where the binary encoded most significant digit on leads 210 and least significant digit on leads 211 are introduced into thumbwheel switch buffers 52. These buffers 52 along with the respective thumbwheel switches 101, 102 and 103 and 104 present to the alarm circuits 53 and 54 respectively the signals for comparison for out of limits oxygen concentration. If either the low alarm circuit 53 or the high alarm circuit 54 detects an out of limit condition either will trigger the oscillator 55. The alarm circuits 53 and 54 are substantially identical employing identical integrated circuits 240 and 241. The alarm driver 56 employs an integrated circuit 260 and transistor 261 providing adequate power to provide warning to nearby attendants.

Audible and visual signals of an out of limit condition are produced by the energization of oscillator 55 and drivers 56 connected to the lamp 105 and sonic alarm 106. The oscillator 55 employs AND gate 250 and integrated circuit 251 and RC network made up of resistance 252 and capacitor 253.

The limit circuitry and alarms may be disabled merely by operating each thumbswitch to zero.

SUMMARY

The circuit described above is particularly significant in that it processes, displays and analyzes for limits the signal in pure digital form. This is in contrast with prior monitor display devices which are analog and even digital monitors employing analog limits. The system provides accuracy at least as great as the sensor and does so while drawing only about 300 microamperes of current. This allows continuous operation for periods of up to six months to be followed by battery change with still current readings being rendered.

In the embodiment disclosed, the following components have been found to meet all of the requirements which I have imposed:

| | | |
|---|---|---|
| sensor cell 11 | C1 or C2 | Teledyne Insts. San Gabriel, Calif. |

-continued

| | | |
|---|---|---|
| indicator 20 | 7543/R blue | Liquid Crystal Displays |
| Transistors 71 | PN 2369A | National Semiconductor |
| Transistors 72, 73, 74 | 2N 5086 | Motorola |
| Comparator 93 | LM 4250 | National Semiconductor |
| IC 96 | 74 COO | " |
| IC's 97, 98, 99 | 74 CO4 | " |
| IC's 202, 203 | CD 4518 | RCA |
| GATES 205, 206 | 74 COO | National Semiconductor |
| Registers 213-4 | CD 4056 | RCA |
| IC's 222-3 | 74C 107 | National Semiconductor |
| IC's 224-5 260 | 74C 907 | " |
| GATE 225 | 74C 86 | " |
| Buffers 52 | MM74C 906N | " |
| Thumbwheel switch assembly 101-4 | ISU-1321 | Interswitch |
| IC's 240-41 | 74C107N | National Semiconductor |
| Oscillator 55 | 74COON | " |
| Transistor 261 | LM4250 CN | " |

The above described embodiments of this invention are merely descriptive of its principles and are not to be considered limiting. The scope of this invention instead shall be determined from the scope of the following claims including their equivalents.

What is claimed is:

1. Battery powered condition sensing and display apparatus for continuous operation at low battery drain and low battery indication comprising:
   a sensor operative to produce an electrical signal proportional to the condition being monitored;
   signal conditioning apparatus including calibration means for adjusting the level of electrical signals from said sensor as a function of a reference standard;
   battery supply means for powering said apparatus;
   means electively connecting the sensor to said apparatus;
   said connecting means including a switch responsive to the connection of said sensor to said apparatus for applying power from said battery supply means to said apparatus and for terminating power to said apparatus upon disconnection of said sensor;
   voltage regulator means forming a part of said battery supply means;
   said voltage regulator means including at least one normally back biased transistor for regulating the voltage to the apparatus with a minimum of current drain when said battery supply means is at greater than a predetermined minimum value;
   an analog to digital converter connected to the output of said signal conditioning apparatus for converting the calibrated signal therefrom into digital form;
   display means for displaying in digital form the output of said analog to digital converter;
   circuit means for monitoring the output voltage of said battery supply means; and means responsive to the sensing of the falloff of battery terminal voltage below a predetermined level for generating and inserting an additional symbol on said display means while maintaining the correct numerical indication on said display.

2. The apparatus in accordance with claim 1 wherein said circuit means for monitoring the output voltage of said battery supply means generating and inserting an indication in said display of an impossible value for the digital readout while maintaining the correct numerical indication thereof.

3. The apparatus in accordance with claim 2 wherein said means responsive to the sensing of the falloff of battery terminal voltage below a predetermined level generates and displays a minus sign along with the numerical indicaton on said display.

4. The apparatus in accordance with claim 1 including means for selecting and encoding in digital form at least one condition limit;
   means for comparing the digital form of calibrated signal with said selected condition limit in digital form; and
   means for energizing an alarm when said digitized calibrated signal exceeds the value of said condition limit as selected and encoded in digital form.

5. The apparatus in accordance with claim 1 wherein said sensor is selectively connected to said apparatus by a connector, the engaging of said connector with said apparatus completing the circuitry to power the apparatus.

* * * * *